United States Patent [19]

Quimby, Jr. et al.

[11] Patent Number: 5,358,863
[45] Date of Patent: Oct. 25, 1994

[54] OIL AND ABSORBENT COATED GRANULES CONTAINING ENCAPSULATED LIVING ORGANISMS FOR CONTROLLING AGRICULTURAL PESTS

[75] Inventors: Paul C. Quimby, Jr.; Jennifer L. Birdsall; Anthony J. Caesar, all of Bozeman, Mont.; William J. Connick, Jr., New Orleans, La.; Clyde D. Boyette, Leland, Miss.; T. Can Caesar; David C. Sands, both of Bozeman, Mont.

[73] Assignee: The United States of America as represented by the Secretary of the Agriculture, Washington, D.C.

[21] Appl. No.: 39,679

[22] Filed: Mar. 30, 1993

[51] Int. Cl.$^5$ .................. C12N 11/10; C12N 11/04; A01N 63/00
[52] U.S. Cl. ..................... 435/178; 424/93.5; 435/177; 435/182; 504/117
[58] Field of Search ......... 435/177, 178, 182; 424/93 Q; 504/117

[56] References Cited

U.S. PATENT DOCUMENTS

| | | | |
|---|---|---|---|
| 4,718,935 | 1/1988 | Walker et al. | 71/79 |
| 4,724,147 | 2/1988 | Marois et al. | 424/93 |
| 4,902,333 | 2/1990 | Quimby, Jr. | 71/79 |
| 5,034,328 | 7/1991 | Boyette | 435/254 |
| 5,074,902 | 12/1991 | Connick, Jr. et al. | 424/93 X |

Primary Examiner—David M. Naff
Attorney, Agent, or Firm—M. Howard Silverstein; John D. Fado

[57] ABSTRACT

Granules of encapsulated living organisms for controlling agricultural pests are provided having a coating of an invert oil that forms a water-in-oil emulsion and an adsorbent for the oil to make the coated granules free-flowing. The oil slows drying of the organisms to maintain vitality of the organisms. The coated granules are produced by encapsulating bacteria, fungi or nematodes that control agricultural pests in alginate, starch or wheat gluten to form granules, coating the granules with a water-in-oil emulsion of the invert oil, coating the granules with the adsorbent for the oil and drying the coated granules to about 1–10% moisture. The adsorbent can be hydrated silica, fumed silica, clay, bran, diatomaceous earth, zeolite, absorbent starch or mixtures thereof.

10 Claims, No Drawings

5,358,863

OIL AND ABSORBENT COATED GRANULES CONTAINING ENCAPSULATED LIVING ORGANISMS FOR CONTROLLING AGRICULTURAL PESTS

FIELD

The present invention pertains to encapsulated bioactive materials.

PRIOR ART

It is well known in the prior art that biocontrol agents, including fungi, bacteria, and nematodes, may be encapsulated in alginate or starch matrices. Wheat gluten also has been employed for encapsulation. Ordinarily, the encapsulated product is in the form of granules (i.e., pellets or particulates), that are dispersed or sprayed directly upon or in the locus of the agricultural pest target such as weeds, insects, diseases and nematodes that are harmful to desirable plants and agricultural crops. The purpose of the biocontrol agent is to control (e.g., reduce the population or growth, or possibly eliminate) the pest target.

One of the problems associated with such encapsulated biocontrol agents is that the granules tend to dry out too quickly, which is harmful to the agent since moisture is necessary to initiate activation thereof. One prior art method for combating this problem is to spray dew or mist on the material after it has been sprayed on or in the vicinity of the target pest. Another method is disclosed in U.S. Pat. No. 4,902,333, wherein the agent is applied to the target from an invert oil emulsion.

SUMMARY

A new encapsulated product has been developed which significantly retards evaporation of water from the granules.

Broadly, the invention comprises coating such granules with a mixture of (a) an invert oil and (b) and adsorbent for such oil. As used herein, the expression "invert oil" or "inverting oil" is in reference to oils that form water-in-oil emulsions. Any unrefined or refined vegetable or paraffinic oil that is nontoxic to the living organism which is encapsulated in the granule may be used. Appropriate oil adsorbents include hydrated silica, fumed silica, kaolin and other clays, corn bran, oat bran, wheat bran and other brans, diatomaceous earth, zeolite and absorbent starch.

Despite the presence of the adsorbent, the oil component unexpectedly slows the drying process of the living agents, whereby the vitality of the agents can be maintained for extended storage periods at 3° C. to −10° C.

The adsorbent further unexpectedly and extensively changes the properties of the granules so that they are flowable and can be easily suspended in aqueous slurries for spraying.

After storage, upon rewetting and application to the target pests, the granules once again undergo unexpected slow drying which allows for activation of the biocontrol agents with minimal dew or mist.

Deposits of such material will retain more than 10% moisture for as long as 8–12 hours.

An object of the present invention is to provide an encapulated biocontrol agent in which viability and storability of fragile biocontrol agents are improved over that of the same organisms formulated in alginate, starch, wheat gluten or clays alone.

Another object of the present invention is to provide a granule that, in an aqueous suspension, is much cleaner and easier to handle than oily invert emulsions.

Still another object is to provide a formulation that can be applied with conventional agricultural sprayers, whereas special sprayers are required for invert emulsions.

Yet another object is to provide a formulation that produces less crop phytotoxicity than is produced by oily invert emulsions.

A further object is to provide a granule wherein the drying phase for production requires no special equipment or control of humidity.

Still a further object is to provide a granule that is slow drying to the degree that enough moisture initially is present at the time of application for initiating activation of the biocontrol agent, whereby dependence on dew or mist is reduced.

Even a further object is to provide a living organism-containing granule that is amenable to long-term refrigerated storage.

Other objects and advantages will be obvious from the following more detailed description of the invention.

DETAILED DESCRIPTION

The product of the present invention may be produced as follows:

The granules first are produced in the prior art manner described, for example, in U.S. Pat. Nos. 4,718,935, 4,724,147 and 5,074,902. As an example, in the production of alginate granules, a mixture of sodium alginate (gel) and kaolin (suspension) is prepared. After sterilizing in an autoclave or microwave, the mixture is cooled before adding the living fermentation product or cell culture (1 part living fermentation product or culture per 1 part mixture of alginate and kaolin).

Thereafter, the living organism-containing mixture is added to a calcium salt solution (0.25M) to form calcium alginate granules. The granules typically contain 0.7%–1.0% sodium alginate and 4.5%–5.5% koalin.

Optionally, the living organism-containing mixture may be extruded as a "string" into the calcium salt solution to form spaghetti-like material, which, either before or after rinsing, may be ground to desired size in a blender filled with 0.25M calcium salt solution or water and operated at slow speed, with the intent to reduce the strings to granules that will be 250–700 microns in size after drying.

The above-described granule formation steps are known in the prior art.

At this stage of the prior art process, the granules normally would be subject to a drying step to remove excess water from the interior thereof. However, in the present invention, the drying step is delayed until a later time. After rinsing the granules, and prior to drying, they are coated with an inverting oil emulsion (water-in-oil) typically having about 1–2 parts water to 4–5 parts oil (v/v) to thoroughly coat the granules with oil. The emulsion is present in an amount that results in about 1 part inverting oil being mixed with 2–4 parts granules (v/v). Hand mixing may be employed.

Many inverting oils may be employed, including soybean oil, sunflower oil, canola oil, refined corn oil, unrefined corn oil, various mineral (petroleum) oils. They may be employed with or without additives including emulsifiers such as lecithin, monoglycerides and lanolin. Other additives include waxes (e.g. paraffin and natural wax such as beeswax) and glycerin to retard further the rate of moisture loss from the granules. With specific regard to glycerin, it protects cell membranes from drying or freezing, and is best incorporated when the granule-forming ingredients initially are mixed together.

The following is a typical recipe for corn oil plus additive:
unrefined corn oil, 58.33% (up to 100%);
mineral oil (e.g., Orchex 796), 19.42% (ranging from 0-20%);
lanolin 10% (ranging from 0-10%);
paraffin, 8.25% (ranging from 0-8.25%, 6% preferred);
monoglyceride (e.g., Myverol 18-92), 4.00% (ranging from 0-5.0%)

Since unrefined corn oil contains its own emulsifying agent (lecithin), it is more suitable to be used without any additives in comparison to refined corn oil.

After coating the granules with inverting oil, oil adsorbent subsequently is applied at the same time that the granule drying step is performed. This may be carried out in a laminar flow hood, to reduce contamination, at room temperature (about 23°), and a relative humidity of about 20%-65%.

The amount of adsorbent depends upon the type of adsorbent. For example, with regard to hydrated silica, typically it is added in an amount of 4 parts adsorbent per part granules, v/v.

Preferably, the adsorbent is added in increments equal to about ⅛ to 1/40 of the total amount of adsorbent, until such time as the granules become free-flowing. It usually takes about 10 to 20 minutes to add the adsorbent in this manner.

The presence of the inverting oil slows down the drying process. For example, the granules will become dried to about 10% moisture in about 12 hours. Thereafter, drying usually is continued for another 12-24 hours, thereby providing a total drying time of 24-48 hours. The final product typically contains about 1 to 10% moisture.

As noted above, the adsorbents include hydrated silica, fumed silica, kaolin and other clays, corn bran, oat bran, wheat bran and other brans, diatomaceous earth, zeolite and absorbent starch, or combinations thereof. A typical combination would be 12 parts corn bran to 7 parts kaolin.

By the process of the present invention, the granules are essentially completely coated by the oil-oil adsorbent mixture. However, if it is desired to reduce the size of the coated product as by milling, then this will result in smaller particles having a partial coating of oil-oil adsorbent mixture.

The thickness of the coating typically will be about 30 to 50 microns.

Any living organisms that previously have been encapsulated in alginate, starch or wheat gluten may be employed in the coated granules of the present invention. Exemplary organisms include plant pathogenic fungi (e.g., Sclerotinia, Rhizoctonia, Fusarium, Alternaria, Colletotrichum, Sclerotium), entomopathogenic fungi (e.g., Pandora, Conidiobolus) plant pathogenic bacteria (e.g., Psuedomonas, Agrobacterium), gall-forming nematode (e.g., Subanquina).

In ongoing storage tests, refrigerated or frozen Fusarium spp. and Sclerotium rolfsii were alive after 16 months. Refrigerated Alternaria alternata was alive after 32 months. One sample of refrigerated Sclerotinia sclerotiorum was alive after 32 months while another sample was dead after 29 months. Frozen S. sclerotiorum was alive after 29 months. Refrigerated Colletotrichum truncatum was dead after 13 months, but frozen C. truncatum was alive after 13 months.

Coated granules of Subanquina picridis from natural and tissue culture galls have been successfully stored at 4° C. and −20° for almost 3 months, with greater than 50% survival. However, in another test, Subanquina picridis from whole galls in the presence of oil died after one month, whereas whole galls without oil still survived (35%) after 3 months, which illustrates that, with regard to nongranule formulations, the presence of oil may be detrimental to storage.

In yet another test, "Coltru" granules of C. truncatum formulated in accordance with the present invention, after 42 hours of drying had 3 times more colony forming units per gram than did those without the inverting oil-oil adsorbent coating.

Some organisms encapsulated in the coated granules of the present invention may be stored at room temperature (20°-25° C.) for 1-4 weeks or longer (e.g., Fusarium spp.) without destroying vitality.

Test data has shown that the inverting oil-oil adsorbent coating greatly slows the evaporation of water in the system during the initial drying phase at room temperature and relative humidity. After six hours of drying, granules were at −40 bars with the coating, vs. −74 bars without the coating. The moisture was slowly evaporated over at least 24 hours in such tests.

The granules may be taken out of storage and applied to the target pest in the prior art manner. For example, they may be suspended in a viscous slurry of water-absorbent starch (e.g., 0.5% w/v "Water-Lok") plus surfactant (e.g., 0.05% v/v "Tween-80"), and, if necessary, a hydrating sugar, e.g., fructose (corn syrup) or molasses at 0.5% to 1% v/v. The resulting slurry can be sprayed through large-orifice nozzles (e.g., disc/core 6/56) without strainers at 15 to 25 psi and at rates of up to 4 g granules/100 ml spray slurry or about 7 lb/A at 20 GPA or about 14 lb/A at 40 GPA.

The following is an exemplary test of the formulation of the present invention: Granules of the present invention containing Sclerotinia sclerotiorum that had been applied to the stems of sunflower seedlings, killed about 50% of the seedlings without any dew. Fresh preparations of the fungus, not as part of the formulation of the present invention, that were applied without dew had no effect.

It should be understood that living organisms are very fragile, and that, even with the advantages achieved by the present invention, some organisms will not be effective against specific targets. Therefore, it is necessary, through routine experimentation, to determine the effectiveness of candidate organisms, formulated in the manner of the present invention, against specific targets.

We claim:

1. Coated granules of encapsulated living organism for controlling agricultural pests, said granules coated with a mixture of (a) an inverting oil that is nontoxic to said living organism and (b) an adsorbent for said oil, wherein said living organism is selected from the group consisting of bacteria, fungi and nematodes; wherein said organism is encapsulated with an encapsulation agent selected from the group consisting of alginate, starch and wheat gluten; wherein said pests are selected from the group consisting of weeds, insects, diseases and nematodes that are harmful to desirable plants; wherein said inverting oil is an oil that forms a water-in-oil emulsion; wherein said absorbent is present in an amount which makes said granules free-flowing and said coated granules containing about 1 to 10% moisture.

2. The granules of claim 1 wherein said oil is selected from the group consisting of vegetable oils, mineral oils and mixtures thereof.

3. The granules of claim 1 wherein said adsorbent is selected from the group consisting of hydrated silica, fumed silica, clay, bran, diatomaceous earth, zeolite, absorbent starch, and mixtures thereof.

4. The granules of claim 2 wherein said absorbent is selected from the group consisting of hydrated silica, fumed silica, clay, bran, diatomaceous earth, absorbent starch, and mixtures thereof.

5. A method of modifying granules of encapsulated living organism for controlling agricultural pests comprising coating said granules with a water-in-oil emulsion whose oil component is an inverting oil that is nontoxic to said living organism; coating said granules with an absorbent for said oil; and drying said granules to remove water therefrom to produce coated granules containing about 1 to 10% moisture; wherein said living organism is selected from the group consisting of bacteria, fungi and nematodes; wherein said encapsulated organism is produced by encapsulation with an encapsulation agent selected from the group consisting of alginate, starch and wheat gluten; wherein said pests are selected from the group consisting of weeds, insects, diseases and nematodes that are harmful to desirable plants; and wherein said absorbent is applied in amount which makes said granules free-flowing.

6. The method of claim 5 wherein said oil is selected from the group consisting of vegetable oils, mineral oils and mixtures thereof.

7. The method of claim 5 wherein said adsorbent is selected from the group consisting of hydrated silica, fumed silica, clay, bran, diatomaceous earth, zeolite, absorbent starch, and mixtures thereof.

8. The method of claim 6 wherein said adsorbent is selected from the group consisting of hydrated silica, fumed silica, clay, bran, diatomaceous earth, zeolite, absorbent starch, and mixtures thereof.

9. Coated granules of encapsulated living organsim for controlling agricultural pests, said granules coated with a mixture consisting essentially of (a) an inverting oil that is nontoxic to said living organism and (b) an adsorbent for said oil, wherein said living organism is selected from the group consisting of bacteria, fungi and nematodes; wherein said organism is encapsulated with an encapsulation agent selected from the group consisting of alginate, starch and wheat gluten; wherein said pests are selected from the group consisting of weeds, insects, diseases and nematodes that are harmful to desirable plants; wherein said inverting oil is an oil that forms a water-in-oil emulsion; wherein said absorbent is present in an amount which makes said granules free-flowing and said coated granules containing about 1 to 10% moisture.

10. The granules of claim 9 wherein said adsorbent is selected from the group consisting of hydrated silica, fumed silica, clay, bran, diatomaceous earth, zeolite, absorbent starch, and mixtures thereof.

* * * * *